(12) United States Patent
Mairs et al.

(10) Patent No.: US 11,596,359 B2
(45) Date of Patent: Mar. 7, 2023

(54) METHODS AND SYSTEMS FOR MITIGATING SENSOR ERROR PROPAGATION

(71) Applicant: MEDTRONIC MINIMED, INC., Northridge, CA (US)

(72) Inventors: Nicholas S. Mairs, Minneapolis, MN (US); Maxwell P. Lundeen, Golden Valley, MN (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 173 days.

(21) Appl. No.: 16/844,726

(22) Filed: Apr. 9, 2020

(65) Prior Publication Data

US 2021/0315525 A1 Oct. 14, 2021

(51) Int. Cl.
*G16H 40/67* (2018.01)
*G16H 50/50* (2018.01)
(Continued)

(52) U.S. Cl.
CPC ........ *A61B 5/7203* (2013.01); *A61B 5/14532* (2013.01); *G16H 10/60* (2018.01);
(Continued)

(58) Field of Classification Search
CPC .. A61B 5/7203; A61B 5/14532; G16H 40/67; G16H 50/50; G16H 10/60; G16H 50/30; G16H 50/20
(Continued)

(56) References Cited

U.S. PATENT DOCUMENTS 4,562,751 A 1/1986 Nason et al.
4,685,903 A 8/1987 Cable et al.
(Continued)

FOREIGN PATENT DOCUMENTS

| CA | 3088255 A1 | 7/2017 |
| CA | 3080719 A1 | 6/2019 |
| WO | 2019118060 A1 | 6/2019 |

OTHER PUBLICATIONS

International Search Report and Written Opinion of the International Searching Authority issued in corresponding application PCT/US2021/022522 dated Jun. 30, 2021 (13 pages).

*Primary Examiner* — Michael Tomaszewski
*Assistant Examiner* — Rachael Sojin Stone
(74) *Attorney, Agent, or Firm* — Weaver Austin Villeneuve & Sampson LLP

(57) ABSTRACT

Medical devices and related systems and methods are provided. A method of providing a notification pertaining to a physiological condition using a translation model involves identifying an error metric associated with an input variable associated with the translation model, determining a reference output of the translation model by providing reference values for the input variable to the translation model, generating modulated values for the input variable based on the reference values using the error metric, determining a simulated output of the translation model by providing the modulated values for the input variable to the translation model, and updating the translation model to reduce a weighting associated with the input variable when a difference between the simulated output and the reference output is greater than a threshold.

20 Claims, 5 Drawing Sheets

(51) Int. Cl.
*G16H 10/60* (2018.01)
*G16H 50/30* (2018.01)
*G16H 50/20* (2018.01)
*A61B 5/00* (2006.01)
*A61B 5/145* (2006.01)

(52) U.S. Cl.
CPC ............ *G16H 40/67* (2018.01); *G16H 50/20* (2018.01); *G16H 50/30* (2018.01); *G16H 50/50* (2018.01)

(58) Field of Classification Search
USPC .......................................................... 705/2
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Mair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 11,445,951 B2 * | 9/2022 | Ajemba ............... A61B 5/1468 |
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2011/0237917 A1 * | 9/2011 | Roy .................. A61B 5/14532 702/19 |
| 2013/0338630 A1 | 12/2013 | Agrawal et al. |
| 2014/0066889 A1 | 3/2014 | Grosman et al. |
| 2017/0156642 A1 | 6/2017 | Sekimoto et al. |
| 2018/0169334 A1 | 6/2018 | Grosman et al. |
| 2021/0174960 A1 * | 6/2021 | Gee ....................... G16H 40/40 |
| 2021/0315525 A1 * | 10/2021 | Mairs ..................... G16H 40/67 |

* cited by examiner

METHODS AND SYSTEMS FOR MITIGATING SENSOR ERROR PROPAGATION

TECHNICAL FIELD

Embodiments of the subject matter described herein relate generally to medical devices, and more particularly, embodiments of the subject matter relate to mitigating the impact of measurement errors for improved patient monitoring and management using sensing devices.

BACKGROUND

Management of diabetes often involves monitoring and regulating a patient's blood glucose level in a substantially continuous manner. Rather than continuously sampling and monitoring a user's blood glucose level, intermittently sensed glucose data samples are often utilized for purposes of continuous glucose monitoring (CGM). The sensed glucose measurement data, in turn, may be utilized to calculate bolus dosages, determine operating commands for an infusion pump, provide recommendations or other insights for managing the patient's condition to the patient, a healthcare provider, and/or the like.

Many CGM sensors measure the glucose in the interstitial fluid (ISF). Typically, to achieve the desired level of accuracy and reliability and reduce the impact of noise and other spurious signals, the sensor data is calibrated using a known good blood glucose value, often obtained via a so-called "fingerstick measurement" using a blood glucose meter that measures the blood glucose in the capillaries. However, performing such calibration measurements increases the patient burden and perceived complexity, and can be inconvenient, uncomfortable, or otherwise disfavored by patients. Moreover, ISF glucose measurements lag behind the blood glucose measurements based on the time it takes glucose to diffuse from the capillary to the interstitial space where it is measured by the CGM sensor, which requires signal processing (e.g., filtering) or other techniques to compensate for physiological lag. Additionally, various factors can lead to transient changes in the sensor output, which may influence the accuracy of the calibration. Degradation of sensor performance over time or manufacturing variations may further compound these problems. Accordingly, it is desirable to account for variations and measurement errors in a manner that decreases the patient burden and improves the overall user experience without compromising accuracy or reliability.

BRIEF SUMMARY

Medical devices and related systems and operating methods are provided. In one embodiment, a method of providing a notification pertaining to a physiological condition using an instance of a sensing element capable of providing electrical signals influenced by the physiological condition in a body of a patient is provided. The method involves identifying an error metric associated with an input variable associated with a translation model, the translation model providing an output that is influenced by a value for the input variable and a weighting associated with the input variable, determining a reference output of the translation model by providing reference values for the input variable to the translation model, generating modulated values for the input variable based on the reference values using the error metric, determining a simulated output of the translation model by providing the modulated values for the input variable to the translation model, and updating the translation model with a reduced weighting associated with the input variable when a difference between the simulated output and the reference output is greater than a threshold. A notification is generated based at least in part on an output of the updated translation model when one or more subsequent values for the input variable derived from one or more electrical signals output by the instance of the sensing element are input to the updated translation model with the reduced weighting.

In another embodiment, a method of monitoring a glycemic condition of a patient using a glucose sensing element providing electrical signals influenced by a glucose level in a body of the patient is provided. The method involves identifying an error metric associated with a variable influenced by the electrical signals provided by the glucose sensing element, determining modulated values for the variable using the error metric, determining a reference output of a translation model using reference values for the variable, wherein the reference output of the translation model is influenced by the reference values and a weighting associated with the variable, and determining a simulated output of the translation model using the modulated values for the variable, wherein the simulated output of the translation model is influenced by the simulated values and the weighting. When a difference between the simulated output and the reference output is greater than a threshold, the method continues by updating the translation model to reduce the difference and providing the updated translation model to a device associated with the patient, wherein the device generates a notification based at least in part on an output of the updated translation model when one or more subsequent values for the variable derived from one or more subsequent electrical signals output by the glucose sensing element in response to the glucose level in the body of the patient are input to the updated translation model.

In another embodiment, a system is provided that includes a database and a server coupled to the database. The database stores historical measurement data corresponding to instances of a sensing element influenced by a physiological condition. The server identifies an error metric associated with an input variable to a translation model based at least in part on the historical measurement data, identifies reference values for the input variable using the historical measurement data, determines modulated values for the input variable based on the reference values using the error metric, determines a reference output of the translation model by providing the reference values for the input variable to the translation model, determines a simulated output of the translation model by providing the modulated values for the input variable to the translation model, and updates the translation model to reduce influence of the input variable when a difference between the simulated output and the reference output is greater than a threshold. A user notification is generated based at least in part on an output of the updated translation model when one or more subsequent values for the input variable derived from one or more electrical signals output by an instance of the sensing element are input to the updated translation model.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
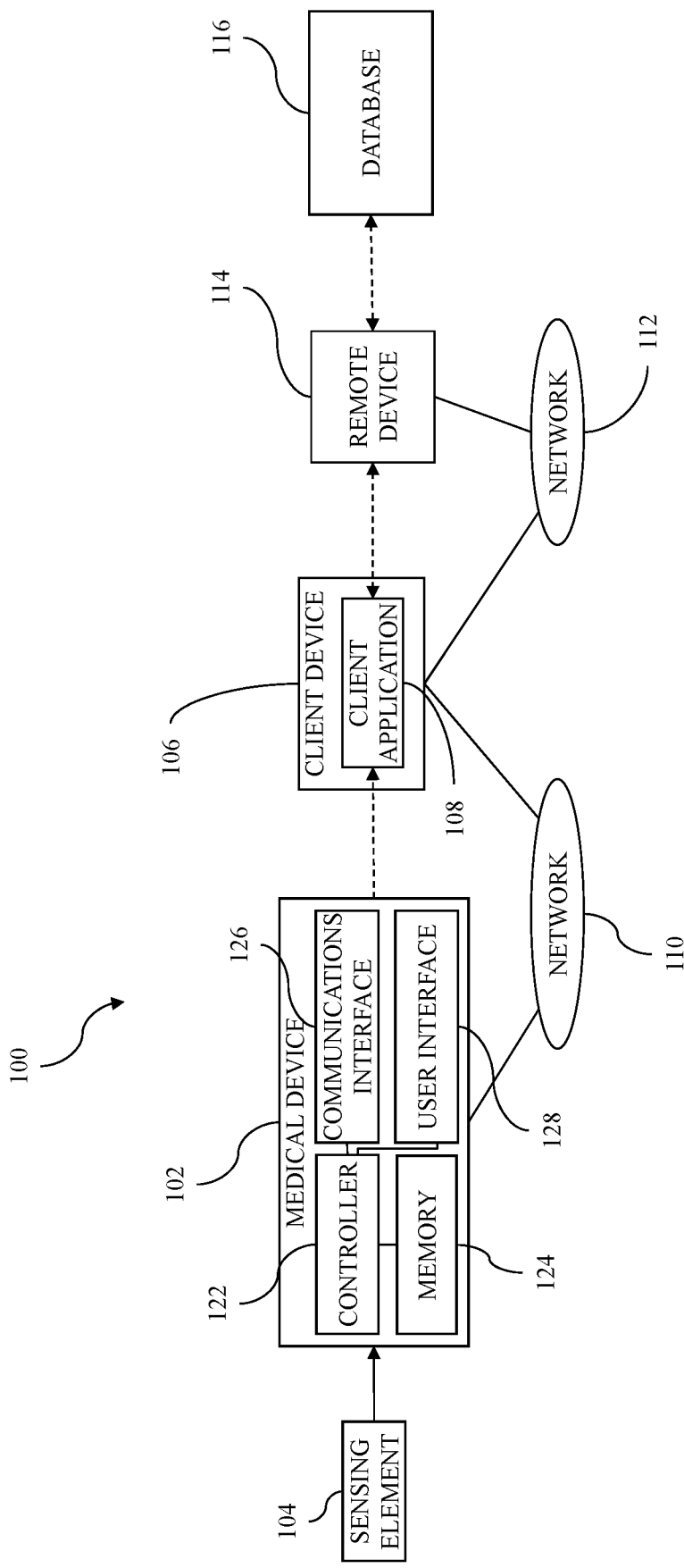
FIG. 1 depicts an exemplary embodiment of a patient monitoring system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein generally relate to sensing elements and related sensing arrangements and devices that provide an output that is indicative of and/or influenced by one or more characteristics or conditions that are sensed, measured, detected, or otherwise quantified by the sensing element. While the subject matter described herein is not necessarily limited to any particular type of sensing application, exemplary embodiments are described herein primarily in the context of a sensing element that generates or otherwise provides electrical signals indicative of and/or influenced by a physiological condition in a body of a human user or patient, such as, for example, interstitial glucose sensing elements.

For purposes of explanation, exemplary embodiments of the subject matter are described herein as being implemented in conjunction with medical devices, such as portable electronic medical devices. Although many different applications are possible, the following description may be described herein primarily in the context of continuous glucose monitoring (CGM) devices or similar patient monitoring devices or systems. That said, the subject matter may be implemented in an equivalent manner in the context of other medical devices, such as, for example, a fluid infusion device (or infusion pump) as part of an infusion system deployment, injection pens (e.g., smart injection pens), and the like. For the sake of brevity, conventional techniques related to glucose sensing, blood glucose meters, sensor calibration, infusion system operation and/or other functional aspects of the systems (and the individual operating components of the systems) may not be described in detail here. It should be noted the subject matter described herein can be utilized generally in the context of overall diabetes management or other physiological conditions independent of or without the use of an infusion device or other medical device (e.g., when oral medication is utilized), and the subject matter described herein is not limited to any particular type of medication. In this regard, the subject matter is not limited to medical applications and could be implemented in any device or application that includes or incorporates a sensing element.

As described in greater detail below, the subject matter described herein facilitates reducing or otherwise mitigating the impact of measurement error, noise, and/or other variations on the output or performance of various translation models that may be applied to the measurements output by a sensing element to gain insights or otherwise provide feedback pertaining to the condition being monitored. In this regard, the translation model could be any sort of equation or function derived for calculating or otherwise translating a set of input variables into a different output variable or representation. For example, an estimation model may be derived using machine learning or other artificial intelligence techniques to obtain an equation or function for calculating an estimated value output by the model (e.g., an estimated glucose value) based on a number of input variables derived from the electrical signal(s) output by a sensing element using different weighting factors or other relative relationships among those respective input variables. As described below, the error associated with one or more input variables to a translation model is utilized to generate a simulated output of the translation model that represents the potential or probable impact of error with respect to a given input variable. Based on the amount by which the error associated with a particular input variable causes the simulated output to deviate from some reference output, the relative weighting of that input variable with respect to the output of the translation model may be reduced or otherwise adjusted to reduce the deviation between the simulated output and the reference output, thereby resulting in an updated version of the translation model with better noise or error immunity with respect to that input variable.

The error mitigation processes described herein may be performed with respect to lower-level translation models, higher-level translation models, or any combination or sequence thereof that may be employed in a given system. For example, in a system that has multiple layers of translation models (e.g., a lower-level glucose estimation model followed by a higher-level classification model that generates a characterization or other feedback or insights using the lower-level glucose estimation model), the error mitigation process may allow for the manner in which the error associated with different lower-level input variables (e.g., input variables to the lower-level glucose estimation model) propagate to impact the higher-level output (e.g., the output of the higher-level classification model) by adjusting the weighting or influence those lower-level input variables or lower-level model outputs have on the higher-level model output. As a result, the higher-level model output is more resilient with respect to measurement errors or other noise, variability or error associated with lower-level variables, thereby providing more representative insights across different operating environments, conditions or scenarios.

Patient Monitoring Overview

FIG. 1 depicts an exemplary embodiment of a patient monitoring system 100 that includes a medical device 102 communicatively coupled to a sensing element 104 that is inserted into the body of a patient or otherwise worn by the patient to obtain measurement data indicative of a physiological condition in the body of the patient, such as a sensed glucose level. In the illustrated embodiment, the medical device 102 is communicatively coupled to a client device 106 via a communications network 110, with the client device 106 being communicatively coupled to a remote device 114 via another communications network 112. In such an embodiment, the client device 106 may function as an intermediary for uploading or otherwise providing measurement data from the medical device 102 to the remote device 114. That said, it should be appreciated that FIG. 1 depicts a simplified representation of a patient monitoring system 100 for purposes of explanation and is not intended to limit the subject matter described herein in any way. For example, some embodiments of a patient monitoring system 100 may support direct communications between the medical device 102 and the remote device 114 via communications network 112. Additionally, practical embodiments of the patient monitoring system 100 may include any number of instances of medical devices 102 and/or client devices 106 to support concurrent monitoring of any number of patients.

The sensing element 104 generally represents the component of the patient monitoring system 100 that is configured to generate, produce, or otherwise output one or more electrical signals indicative of a physiological condition that is sensed, measured, or otherwise quantified by the sensing element 104 (e.g., sensing element 204). In this regard, the physiological condition of a patient influences a characteristic of the electrical signal output by the sensing element 104, such that the characteristic of the output signal corresponds to or is otherwise correlative to the physiological condition that the sensing element 104 is sensitive to. In exemplary embodiments, the sensing element 104 is realized as an interstitial glucose sensing element inserted at a location on the body of the patient that generates an output electrical signal having a current (or voltage) associated therewith that is correlative to or otherwise influenced by the interstitial fluid glucose level that is sensed or otherwise measured in the body of the patient by the sensing element 104.

The medical device 102 generally represents the component of the patient monitoring system 100 that is communicatively coupled to the output of the sensing element 104 to receive or otherwise obtain the measurement data samples from the sensing element 104, store or otherwise maintain the measurement data samples, and upload or otherwise transmit the measurement data to the server 114 via the client device 106. In one or more embodiments, the medical device 102 is realized as a standalone sensing or monitoring device, such as, for example, a continuous glucose monitor (CGM), an interstitial glucose sensing arrangement, or similar device. In this regard, it should be noted that although FIG. 1 depicts the medical device 102 and the sensing element 104 as separate components, in practice, the medical device 102 and the sensing element 104 may be integrated or otherwise combined to provide a unitary device that can be worn by the patient. That said, in other embodiments, the medical device 102 could be realized as an infusion device configured to deliver a fluid, such as insulin, to the body of the patient.

In exemplary embodiments, the medical device 102 includes a controller 122, a data storage element 124 (or memory), a communications interface 126, and a user interface 128. The user interface 128 generally represents the input user interface element(s) and/or output user interface element(s) associated with the medical device 102. The controller 122 generally represents the hardware, circuitry, logic, firmware and/or other component(s) of the medical device 102 that is coupled to the sensing element 104 to receive the electrical signals output by the sensing element 104 and perform or otherwise support various additional tasks, operations, functions and/or processes described herein. Depending on the embodiment, the controller 122 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the controller 122 includes an analog-to-digital converter (ADC) or another similar sampling arrangement that samples or otherwise converts an output electrical signal received from the sensing element 104 into corresponding digital measurement data value. In other embodiments, the sensing element 104 may incorporate one or more ADCs and output one or more digital measurement values.

The communications interface 126 generally represents the hardware, circuitry, logic, firmware and/or other components of the medical device 102 that are coupled to the controller 122 for outputting data and/or information from/to the medical device 102 to/from the client device 106. For example, the communications interface 126 may include or otherwise be coupled to one or more transceiver modules capable of supporting wireless communications between the medical device 102 and the client device 106. In exemplary embodiments, the communications interface 126 is realized as a Bluetooth transceiver or adapter configured to support Bluetooth Low Energy (BLE) communications.

In exemplary embodiments, the client device 106 is realized as a mobile phone, a smartphone, a tablet computer, or other similar mobile electronic device; however, in other embodiments, the client device 106 may be realized as any sort of electronic device capable of communicating with the medical device 102 via network 110, such as a laptop or notebook computer, a desktop computer, or the like. In exemplary embodiments, the network 110 is realized as a Bluetooth network, a ZigBee network, or another suitable personal area network. That said, in other embodiments, the network 110 could be realized as a wireless ad hoc network, a wireless local area network (WLAN), or local area network (LAN). In exemplary embodiments, the client device 106 includes or is coupled to a display device, such as a monitor, screen, or another conventional electronic display, capable of graphically presenting data and/or information pertaining to the physiological condition of the patient. The client device 106 also includes or is otherwise associated with a user input device, such as a keyboard, a mouse, a touchscreen, or the like, capable of receiving input data and/or other information from the user of the client device 106.

In some embodiments, a user, such as the patient, the patient's doctor or another healthcare provider, or the like, manipulates the client device 106 to execute a client application 108 that supports communicating with the medical device 102 via the network 110. In this regard, the client application 108 supports establishing a communications session with the medical device 102 on the network 110 and receiving data and/or information from the medical device 102 via the communications session. The medical device 102 may similarly execute or otherwise implement a corresponding application or process that supports establishing the communications session with the client application 108. The client application 108 generally represents a software module or another feature that is generated or otherwise implemented by the client device 106 to support the processes described herein. Accordingly, the client device 106 generally includes a processing system and a data storage element (or memory) capable of storing programming instructions for execution by the processing system, that, when read and executed, cause processing system to create, generate, or otherwise facilitate the client application 108 and perform or otherwise support the processes, tasks, operations, and/or functions described herein. Depending on the embodiment, the processing system may be implemented using any suitable processing system and/or device, such as, for example, one or more processors, central processing units (CPUs), graphics processing units (GPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 106 and the medical device 102 establish an association (or pairing) with one another over the network 110 to support subsequently establishing a point-to-point communications session between the medical device 102 and the client device 106 via the network 110. For example, in accordance with one embodiment, the network 110 is realized as a Bluetooth network, wherein the medical device 102 and the client device 106 are paired with one another (e.g., by obtaining and storing network identification information for one another) by performing a discovery procedure or another suitable pairing procedure. The pairing information obtained during the discovery procedure allows either of the medical device 102 or the client device 106 to initiate the establishment of a secure communications session via the network 110.

In one or more exemplary embodiments, the client application 108 is also configured to store or otherwise maintain a network address and/or other identification information for the remote device 114 on the second network 112. In this regard, the second network 112 may be physically and/or logically distinct from the network 110, such as, for example, the Internet, a cellular network, a wide area network (WAN), or the like. The remote device 114 generally represents a server or other computing device configured to receive and analyze or otherwise monitor measurement data, event log data, and potentially other information obtained for the patient associated with the medical device 102. In exemplary embodiments, the remote device 114 is coupled to a database 116 configured to store or otherwise maintain data associated with individual patients. In practice, the remote device 114 may reside at a location that is physically distinct and/or separate from the medical device 102 and the client device 106, such as, for example, at a facility that is owned and/or operated by or otherwise affiliated with a manufacturer of the medical device 102. For purposes of explanation, but without limitation, the remote device 114 may alternatively be referred to herein as a server.

It should be noted that in some embodiments, some or all of the functionality and processing intelligence of the remote computing device 114 can reside at the medical device 102 and/or at other components or computing devices that are compatible with the patient monitoring system 100. In other words, the patient monitoring system 100 need not rely on a network-based or a cloud-based server arrangement as depicted in FIG. 1, although such a deployment might be the most efficient and economical implementation. These and other alternative arrangements are contemplated by this disclosure. To this end, some embodiments of the system 100 may include additional devices and components that serve as data sources, data processing units, and/or recommendation delivery mechanisms. For example, the system 100 may include any or all of the following elements, without limitation: computer devices or systems; patient monitors; healthcare provider systems; data communication devices; and the like.

In exemplary embodiments, the remote device 114 receives, from the client device 106, measurement data values associated with a particular patient (e.g., sensor glucose measurements, acceleration measurements, and the like) that were obtained using the sensing element 104, and the remote device 114 stores or otherwise maintains the historical measurement data in the database 116 in association with the patient (e.g., using one or more unique patient identifiers). Additionally, the remote device 114 may also receive, from or via the client device 106, meal data or other event log data that may be input or otherwise provided by the patient (e.g., via client application 108) and store or otherwise maintain historical meal data and other historical event or activity data associated with the patient in the database 116. In this regard, the meal data may include, for example, a time or timestamp associated with a particular meal event, a meal type or other information indicative of the content or nutritional characteristics of the meal, and an indication of the size associated with the meal. In exemplary embodiments, the remote device 114 may also receive historical fluid delivery data corresponding to basal or bolus dosages of fluid delivered to the patient by an infusion device, injection pen, or the like. For example, the client application 108 may communicate with an infusion device to obtain insulin delivery dosage amounts and corresponding timestamps from the infusion device, and then upload the insulin delivery data to the remote device 114 for storage in association with the particular patient. The remote device 114 may also receive geolocation data and potentially other contextual data associated with a device 102, 106 from the client device 106 and/or client application 108, and store or otherwise maintain the historical operational context data in association with the particular patient. In this regard, one or more of the devices 102, 106 may include a global positioning system (GPS) receiver or similar modules, components or circuitry capable of outputting or otherwise providing data characterizing the geographic location of the respective device 102, 106 in real-time.

Figure 2:
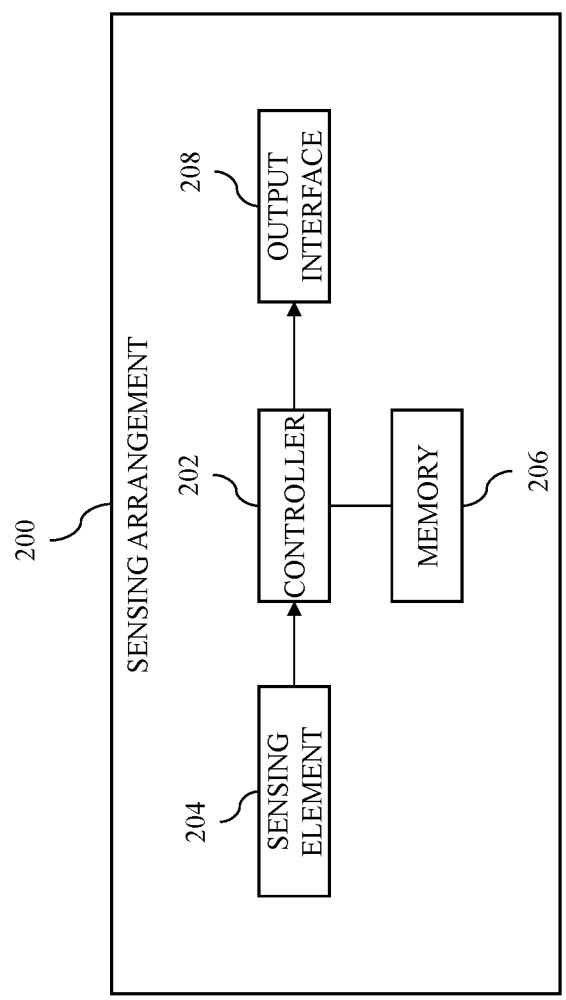
FIG. 2 is a block diagram of an exemplary embodiment of a sensing arrangement suitable for use in the patient monitoring system of FIG. 1.

FIG. 2 depicts an exemplary embodiment of a sensing arrangement 200 suitable for use as the medical device 102 in the patient monitoring system 100 of FIG. 1 in accordance with one or more embodiments. In this regard, FIG. 2 depicts an embodiment where the sensing element 104 is integrated with the medical device 102. The illustrated sensing device 200 includes, without limitation, a controller 202, a sensing element 204 (e.g., sensing element 104), an output interface 208, and a data storage element (or memory) 208. The controller 202 is coupled to the sensing element 204, the output interface 208, and the memory 206, and the controller 202 is suitably configured to support the operations, tasks, and/or processes described herein.

The sensing element 204 generally represents the component of the sensing device 200 that is configured to generate, produce, or otherwise output one or more electrical signals indicative of a condition that is sensed, measured, or otherwise quantified by the sensing device 200. In this regard, the physiological condition of a user influences a characteristic of the electrical signal output by the sensing element 204, such that the characteristic of the output signal corresponds to or is otherwise correlative to the physiological condition that the sensing element 204 is sensitive to. The sensing element 204 may be realized as a glucose sensing element that generates an output electrical signal having a current (or voltage) associated therewith that is correlative to the interstitial fluid glucose level that is sensed or otherwise measured in the body of the patient by the sensing arrangement 200.

Still referring to FIG. 2, the controller 202 generally represents the hardware, circuitry, logic, firmware and/or other component(s) of the sensing device 200 that is coupled to the sensing element 204 to receive the electrical signals output by the sensing element 204 and perform various additional tasks, operations, functions and/or processes described herein. For example, the controller 202 may filter, analyze or otherwise process the electrical signals received from the sensing element 204 to obtain a measurement value for conversion into a calibrated measurement of the interstitial fluid glucose level. Additionally, in one or more embodiments, the controller 202 also implements or otherwise executes a calibration application that calculates or otherwise determines calibrated measurement parameters based on the measurement value using calibration data associated with the sensing element 204 that is stored or otherwise maintained in the memory 206, as described in greater detail below. The calibrated measurement parameters may then be utilized to obtain a calibrated measurement value for the patient's interstitial glucose level.

Depending on the embodiment, the controller 202 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the controller 202, or in any practical combination thereof. In exemplary embodiments, the controller 202 includes or otherwise accesses the data storage element or memory 206. The memory 206 may be realized using any sort of RAM, ROM, flash memory, registers, hard disks, removable disks, magnetic or optical mass storage, short or long term storage media, or any other non-transitory computer-readable medium capable of storing programming instructions, code, or other data for execution by the controller 202. The computer-executable programming instructions, when read and executed by the controller 202, cause the controller 202 to perform the tasks, operations, functions, and processes described in greater detail below.

In some embodiments, the controller 202 includes an analog-to-digital converter (ADC) or another similar sampling arrangement that samples or otherwise converts the output electrical signal received from the sensing element 204 into one or more corresponding digital measurement data values correlative to the interstitial fluid glucose level sensed by the sensing element 204. For example, in various embodiments, the controller 202 may sample, capture, or otherwise analyze the output electrical signal to obtain one or more output measurement values influenced by a glucose concentration in the interstitial fluid compartment of a patient, which may include one or more of an electrical current output by the sensing element 204, electrochemical impedance spectroscopy (EIS) values (for one or more frequencies) or other measurements indicative of a characteristic impedance associated with the sensing element 204, a voltage difference between electrodes or terminals of the sensing element 204 (alternatively referred to herein as the counter electrode voltage (Vctr)), and/or the like. For example, a controller 202 may include hardware and firmware cooperatively configured to collect electrical current measurements corresponding to the electrical current through the sensing element 204, while also calculating the counter electrode voltage (Vctr) and performing electrochemical impedance spectroscopy at various time intervals and at multiple frequencies with respect to the electrical current and voltage. In other embodiments, the sensing element 204 may incorporate one or more ADCs and output one or more digital measurement values based on an analog electrical signal from the sensing element 204.

The output interface 208 generally represents the hardware, circuitry, logic, firmware and/or other components of the sensing arrangement 200 that are coupled to the controller 202 for outputting data and/or information from/to the sensing device 200, for example, to/from the client device 106 and/or the remote device 114. In this regard, in one or more exemplary embodiments, the output interface 208 is realized as a communications interface configured to support communications to/from the sensing device 200. In such embodiments, the communications interface 208 may include or otherwise be coupled to one or more transceiver modules capable of supporting wireless communications between the sensing device 200 and another electronic device (e.g., client device 106). Alternatively, the communications interface 208 may be realized as a port that is adapted to receive or otherwise be coupled to a wireless adapter that includes one or more transceiver modules and/or other components that support the operations of the sensing device 200 described herein. In other embodiments, the communications interface 208 may be configured to support wired communications to/from the sensing device 200. In yet other embodiments, the output interface 208 may include or otherwise be realized as an output user interface element, such as a display element (e.g., a light-emitting diode or the like), a display device (e.g., a liquid crystal display or the like), a speaker or another audio output device, a haptic feedback device, or the like, for providing notifications or other information to the user. In such embodiments, the output user interface 208 may be integrated with the sensing arrangement 200 (e.g., within a common housing) or implemented separately.

It should be understood that FIG. 2 is a simplified representation of a sensing device 200 for purposes of explanation and is not intended to limit the subject matter described herein in any way. In this regard, although FIG. 2 depicts the various elements residing within the sensing device 200, one or more elements of the sensing device 200 may be distinct or otherwise separate from the other elements of the sensing device 200. For example, the sensing element 204 may be separate and/or physically distinct from the controller 202 and/or the communications interface 208. Furthermore, features and/or functionality of described herein as implemented by the controller 202 may alternatively be implemented at another device within a patient monitoring system.

Figure 3:
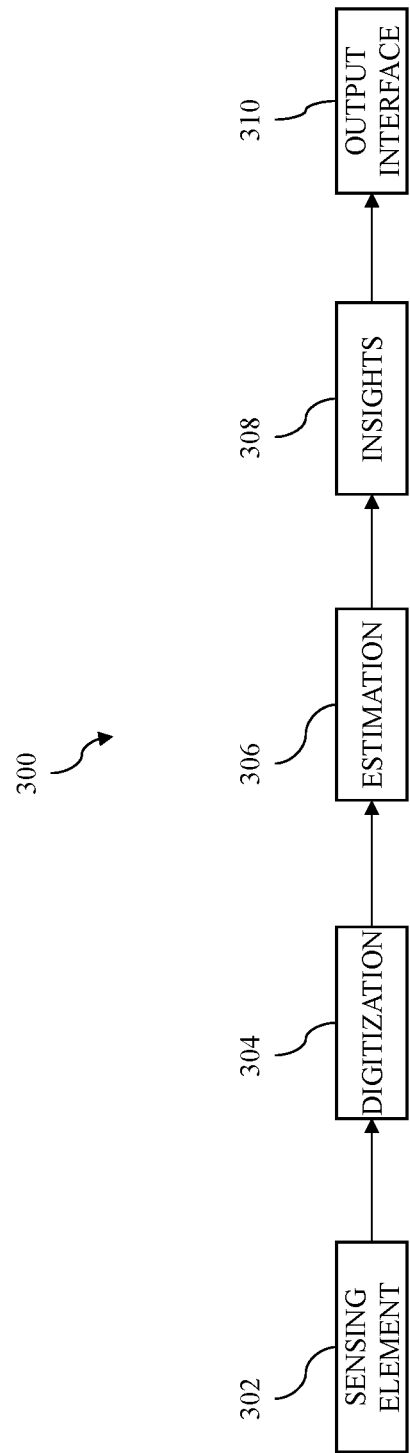
FIG. 3 is a block diagram of an exemplary embodiment of a condition analysis system suitable for implementation in connection with the patient monitoring system of FIG. 1 or the sensing arrangement of FIG. 2.

FIG. 3 depict an exemplary block diagram of a condition analysis system 300 that may be implemented by or within the patient monitoring system 100 for providing recommendations, feedback, or other insights regarding a patient's physiological condition. In this regard, the condition analysis system 300 includes a sensing element 302 (e.g., sensing element 104, 204) having an output that is coupled to a digitizer 304 that is configured to convert, translate, or otherwise transform one or more electrical output signals from the sensing element 302 into one or more corresponding digital measurement parameter values. The output of the digitizer 304 is provided to an estimation module 306 that is configured to receive the one or more digital measurement parameter values from the digitizer 304 and convert, translate, or otherwise transform the digital measurement parameter value(s) into an estimated measurement value for the physiological condition of the patient. The output of the estimation module 306 is provided to an insights engine 308 that analyzes the estimated measurement value and potentially other data and/or information to generate insights, summaries, synopses, recommendations, or other feedback pertaining to one or more aspects of the patient's physiological condition, which, in turn, may be provided to the patient, a healthcare provider, or other user via an output interface 310 (e.g., user interface 128 or output interface 208). For example, the insights engine 308 may generate a user notification with feedback regarding the impact of meals, boluses, exercise, sleep, or any other activity by the patient on the patient's physiological condition (e.g., "Your meal for lunch had a negative impact on your glucose," "Your body has reacted well to a good night of sleep and exercise," etc.).

In exemplary embodiments, one or more of the components 304, 306, 308 may be implemented by or at a sensing device 102, 200, while other components 304, 306, 308 are implemented by or at another device 106, 114 within the patient monitoring system 100. Similarly, the output interface 310 may be associated with any device 102, 106, 114, which itself may or may not implement one or more of the components 304, 306, 308. For example, in one embodiment, the digitization and estimation components 304, 306 are implemented by or at the sensing device 102, 200 (e.g., by controller 122, 202), which outputs or otherwise provides an estimated measurement value to the client device 106 and/or the remote device 114, with the insights engine 308 being implemented by or at one of the client device 106 or the remote device 114. The resulting insights, recommendations, or other notifications generated by the insights engine 308 being implemented by or at one of the client device 106 or the remote device 114 may then be presented by the client application 108 at the client device 106 or by the sensing device 102, 200 (e.g., via user interface 128, 208). That said, in some embodiments, the entirety of the condition analysis system 300 could be implemented by or at the sensing device 102, 200. Accordingly, it should be appreciated that the subject matter described herein is not intended to be limited to any particular system or architecture for implementing the condition analysis system 300. Additionally, while the condition analysis system 300 and related subject matter described herein is not limited to glucose or diabetes, for purposes of explanation, the condition analysis system 300 may be described primarily in the context of providing recommendations, feedback, or other insights regarding a diabetic patient's glycemic condition based on interstitial glucose measurements.

Still referring to FIG. 3, and with reference to FIGS. 1-2, in one or more exemplary embodiments, in the context of an interstitial glucose sensing element 104, 204, 302 utilized in connection with a diabetic patient, the digitizer 304 generally represents the ADCs and other electronics components that are coupled to the interstitial glucose sensing element 104, 204, 302 to sample, capture or otherwise process the analog electrical output signals produced or otherwise provided by the sensing element 104, 204, 302 in response to an interstitial fluid glucose concentration and convert those analog electrical signals influenced by the patient's interstitial fluid glucose level into corresponding digital measurement parameter values. For example, the digitizer 304 may sample the current flow through the interstitial glucose sensing element 104, 204, 302 and the voltage at one or more electrodes or terminals of the sensing element 104, 204, 302 and then analyze or otherwise process the sampled digital values to generate measured values for the electrical current through the sensing element 104, 204, 302 (or isig), the counter electrode voltage (Vctr), and one or more EIS values.

The estimation module 306 generally represents the software, firmware, hardware and/or other electronics that receives the digital measurement parameter values from the digitizer 304 and converts the digital measurement parameter values into an estimated glucose measurement value for the patient. In this regard, the estimation module 306 may implement or otherwise support an algorithm that calculates or otherwise determines an estimated glucose measurement as a function of one or more of the measured electrical current (isig), the counter electrode voltage (Vctr) and measured EIS values. In one embodiment, the estimation module 306 utilizes a model that is derived using machine learning or other artificial intelligence techniques. For example, referring to FIG. 1, the remote server 114 or another computing device in a patient monitoring system 100 may utilize a neural network or other machine learning or artificial intelligence techniques to determine which combination of digital measurement parameter values from the digitizer 304 are correlated to or predictive of the interstitial fluid glucose concentration based on relationships between sets of reference blood glucose measurement values and corresponding contemporaneous combinations of measurement parameter values that may be stored or otherwise maintained in the database 116 (e.g., as historical patient data). The remote server 114 may then determine a corresponding equation, function, or model for calculating an estimated glucose measurement value as a function of those correlative measurement parameter values by optimizing the weighting factors assigned to the measurement parameter values and/or relationships between measurement parameter values to minimize a cost function corresponding to the cumulative differences between the model-predicted glucose measurement value and the reference blood glucose measurement values. The remote server 114 may store or otherwise maintain the data defining the glucose estimation model in the database 116 and transmit or otherwise provide the glucose estimation model data to other devices 102, 106 for implementation of the glucose estimation model at those devices 102, 106.

The insights engine 308 generally represents the software, firmware, hardware and/or other electronics that receives the estimated glucose measurement value for the patient and analyzes the estimated glucose measurement value in connection with other patient data (e.g., insulin delivery data, meal data, exercise data, sleep data, geolocation data, event log data and/or other historical or contextual patient data) to generate one or more recommendations, summaries, analyses, and/or other insights regarding the patient's glycemic condition. In this regard, the insights engine 308 may employ one or more insight models that characterize the glycemic condition of the patient as a function of the estimated glucose measurement value provided by the glucose estimation model 306. The insight model may be similarly derived using machine learning or other artificial intelligence techniques. For example, a neural network or other machine learning or artificial intelligence techniques to determine which combination of estimated glucose measurement values output by the glucose estimation model 306 and other contextual patient data (e.g., meal data, exercise data, sleep data, and/or other activity or event log data) are correlated to or predictive of a particular glycemic condition or state of the patient. In this regard, in some embodiments, the insight model may classify an aspect of the patient's glycemic condition into one of a number of potential classifications substantially in real-time based on the current or most recent estimated glucose measurement values and the historical, recent, concurrent, and/or contemporaneous contextual data associated with the patient. Based on relationships between sets of estimated glucose measurement values and their associated or corresponding patient outcomes and/or contextual data, the remote server 114 may identify which contextual data variables are correlative to a particular glycemic state or outcome in conjunction with the glucose estimation model output, and then determine a corresponding equation, function, or model for calculating or otherwise determining a characterization of the patient's glycemic condition as a function of the glucose estimation model output and correlative contextual data by optimizing the weighting factors assigned to those variables to minimize a cost function corresponding to the cumulative differences between the model-predicted outcome and the observed patient outcomes.

Sensor Measurement Error Mitigation

Figure 4:
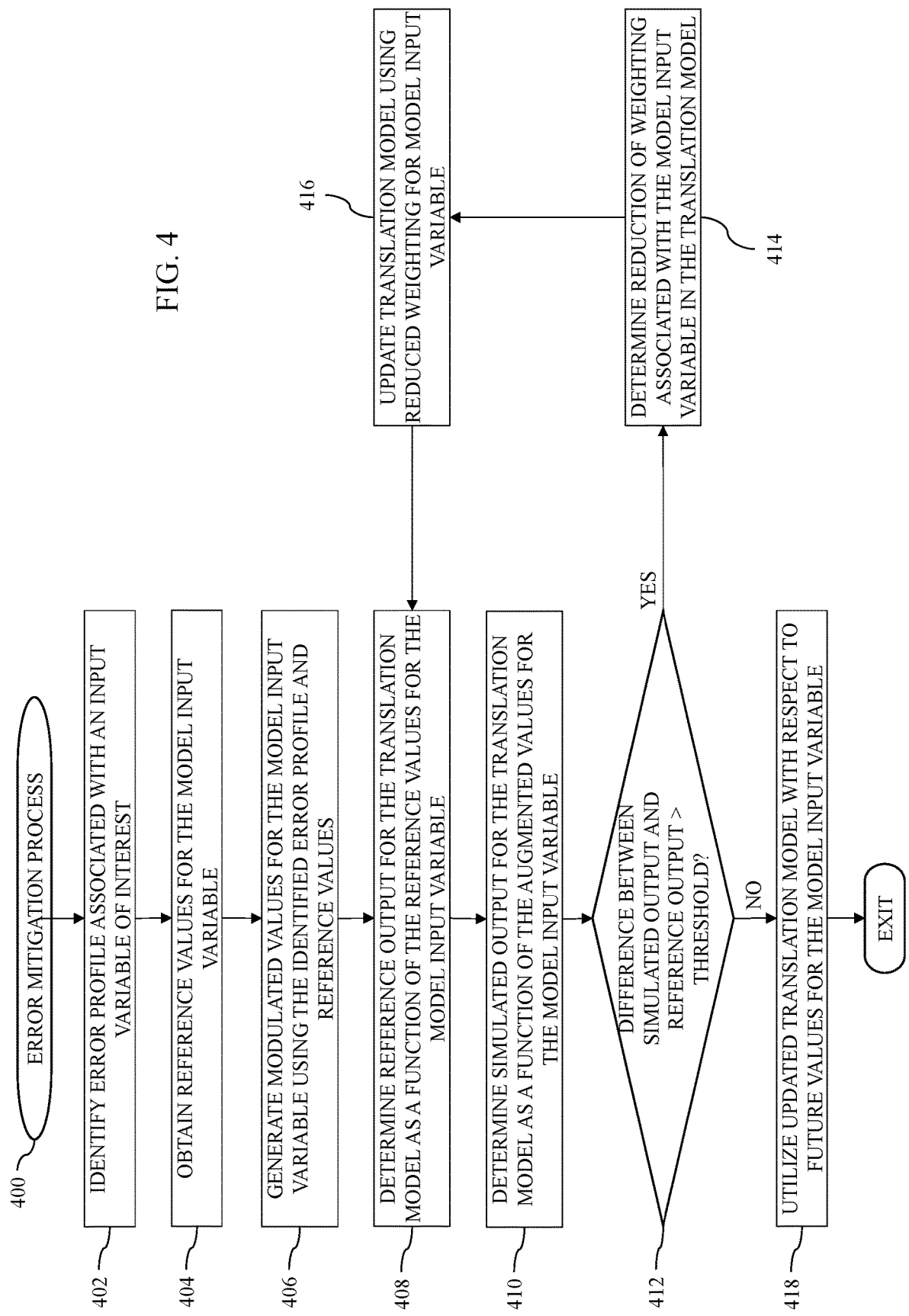
FIG. 4 is a flow diagram of an exemplary error mitigation process suitable for use with the condition analysis system of FIG. 3 in one or more exemplary embodiments.

FIG. 4 depicts an exemplary embodiment of an error mitigation process 400 suitable for implementation in connection with a sensing device or patient monitoring system to mitigate the impact or effect of various sources of measurement error. In this regard, manufacturing variations, material or component variations, electromagnetic interference, and/or other factors may introduce noise or error into a measurement signal, which, in turn, may be propagated with the measurement and reduce the accuracy or reliability of subsequent analysis of the measurement. For example, referring to FIGS. 1-3, manufacturing variances with respect to a sensing element 104, 204, 302 may influence the relationship between the analog electrical output signals produced or otherwise provided by the respective sensing element 104, 204, 302 and a particular interstitial fluid glucose concentration, which, in turn, may introduce noise or error into one or more of the output measurement parameters determined based on those electrical signals (e.g., by digitizer 304). Measurement error in the measurement parameters may, in turn, introduce error into the glucose measurement value determined based thereon, which, in turn, may impact the accuracy or reliability of the analysis of the glucose measurement value and the corresponding recommendations, summaries, insights and/or the like.

While it is often possible to reduce manufacturing variations, doing so can be costly and fail to produce the desired performance improvement due to other external or environmental sources of measurement error. Accordingly, the error mitigation process 400 and related subject matter described herein reduces or otherwise mitigates the effects of measurement error without increasing manufacturing or hardware costs associated with the sensing element 104, 204, 302 or other electronics of the sensing device 102, 200. As described in greater detail below, the error mitigation process 400 identifies one or more input variables to a translation model for which the output of the translation model is susceptible to error. The error mitigation process 400 then reduces the weighting or influence of the input variable(s) to the translation model and dynamically updates or otherwise redevelops the translation model by reoptimizing the weighting factors assigned to other input variables while maintaining fixed the reduced weighting assigned to the identified variable. As a result, the output of the updated translation model may be immune from error with respect to the identified variable of interest, thereby improving the accuracy or reliability of the translation model. Additionally, in some cases, the reduction of the importance of or the elimination of input variables to a translation model may be backwards propagated to the design or manufacturing of the sensing element 104, 204, 302 (e.g., by relaxing manufacturing tolerances or requirements) or other hardware preceding the translation model to achieve further costs savings. For example, if the glucose estimation model utilized by the estimation module 306 does not require any EIS values, the digitizer 304 may be simplified by eliminating any hardware, firmware, software and/or other components that would otherwise have been utilized solely for determining EIS values. While the error mitigation process 400 may be described herein primarily in the context of FIGS. 1-3 and monitoring the glycemic condition of a diabetic patient, it should be appreciated that the error mitigation process 400 is not limited to glucose sensing, glucose measurements, CGM, diabetes management, or the like, and in practice, the error mitigation process 400 may be implemented in an equivalent manner in the context of any type of sensing element or monitoring system.

The various tasks performed in connection with the error mitigation process 400 may be performed by hardware, firmware, software executed by processing circuitry, or any combination thereof. For illustrative purposes, the following description may refer to elements mentioned above in connection with FIGS. 1-3. It should be appreciated that the error mitigation process 400 may include any number of additional or alternative tasks, the tasks need not be performed in the illustrated order and/or the tasks may be performed concurrently, and/or the error mitigation process 400 may be incorporated into a more comprehensive procedure or process having additional functionality not described in detail herein. Moreover, one or more of the tasks shown and described in the context of FIG. 4 could be omitted from a practical embodiment of the error mitigation process 400 as long as the intended overall functionality remains intact.

Referring to FIG. 4, with continued reference to FIGS. 1-3, the illustrated error mitigation process 400 initializes or otherwise begins by identifying or otherwise obtaining an error profile associated with an input variable of interest to be analyzed with respect to a translation model of interest (or a combination or sequence of translation models) that is the subject of the error mitigation process (task 402). In this regard, a translation model utilized to analyze a particular condition is identified, selected or otherwise chosen for error immunization or mitigation, with a respective one of the input variables to the selected translation model (or an input variable to a translation model preceding the selected translation model) being identified, selected or otherwise chosen for further analysis. When the selected translation model is downstream of another translation model (e.g., the glucose estimation model implemented by the estimation module 306 or a translation model implemented by the digitizer 304), the error mitigation process 400 may be performed with respect to input variables to the upstream model. In one embodiment, an administrator may command, signal, or otherwise instruct the remote server 114 to initiate or otherwise perform the error mitigation process 400 with respect to a particular an insight model to be implemented by the insights engine 308 that was previously developed. That said, in other embodiments, the error mitigation process 400 may be automatically performed as a post-process after developing new translation model or updating an existing translation model to provide better noise or error immunity or otherwise improve robustness before deploying the model. After identifying the translation model, the remote server 114 may select or otherwise identify one of the input variables to the translation model for analysis.

In one or more exemplary embodiments, the remote server 114 calculates or otherwise determines the error profile for the selected variable of interest based on data maintained in the database 116. In this regard, the error profile includes one or more error metrics indicative of the measurement error, noise, or other variability associated with the input variable. Depending on the embodiment, the error profile could include one or more of a standard deviation associated with the input variable, a probability distribution associated with the input variable, or a normal distribution for the input variable, and/or the like. For example, when the input variable of interest is measured electrical current (isig), the remote server 114 may calculate the error profile based on relationships between estimated sensor glucose measurement values calculated based on the measured electrical current and corresponding reference blood glucose measurement data maintained in the database 116. In yet other embodiments, the error profile may be calculated or otherwise determined during manufacturing or fabrication of the sensing element 104, 204, 302. For example, instances of the sensing element 104, 204, 302 may be exposed to the same reference glucose concentration, with the different electrical signals output by the different instances of the sensing element 104, 204, 302 for the same reference glucose concentration being analyzed to determine an error profile for a given type, configuration, make and/or model of the sensing element 104, 204, 302.

After identifying an error profile for the input variable of interest, the error mitigation process 400 retrieves or otherwise obtains reference values for the input variable of interest and generates modulated values for the input variable based on the reference values using the error profile (tasks 404, 406). In this regard, the error profile is utilized to vary, dither or otherwise introduce perturbations into the reference values to produce modulated values from the reference values, with the modulated values simulating potential measurement error with respect to the input variable. For example, when the input variable of interest is the measured electrical current (isig), the remote server 114 may obtain historical measured electrical current (isig) values previously and consensually obtained for different patients from the database 116 and calculate or otherwise determine modulated electrical current values that deviate from the historical values in a manner that reflects the probable or likely range of potential deviations given the associated error profile (e.g., using a Monte Carlo simulation based on historical distributions of the measured electrical current).

Still referring to FIG. 4, the error mitigation process 400 continues by calculating or otherwise determining a reference output for the translation model using the reference values for the input variable (task 408). In this regard, the historical or current measurement values for the input variable may be input or otherwise provided to a translation model, along with any other contemporaneous or related historical or actual values for other input variables not currently being analyzed, with the translation model then calculating or otherwise determining an output based on the input combinations of the reference values for the input variable and the contemporaneous or concurrent values for other input variables. For example, reference values for the measured electrical current (isig) may be input or otherwise provided to the glucose estimation model utilized by the estimation module 306 along with the concurrent values for the other measurement parameters output by the digitizer 304 to obtain a reference set of estimated measurement values for the glucose estimation model. In embodiments where the error mitigation process 400 is being performed with respect to an insight model downstream of the glucose estimation model, the reference set of estimated measurement values may be input or otherwise provided to the insight model, which, in turn, is utilized to calculate or otherwise determine reference output data for the insight model as a function of the reference estimated measurement values and the corresponding historical or actual values for other input variables to the insight model (e.g., concurrent or contemporaneous meal data or other event log data).

In a similar manner, the error mitigation process 400 continues by calculating or otherwise determining a simulated output for the translation model using the modulated values for the input variable (task 410). In this regard, the modulated values for the input variable are input or otherwise provided to a translation model while the values for other input variables to the translation model variables not currently being analyzed are maintained the same as were used for determining the reference output. For example, modulated values for the electrical current may be input or otherwise provided to the glucose estimation model utilized by the estimation module 306 along with the concurrent values for the other measurement parameters output by the digitizer 304 to obtain a simulated set of measurement values for the glucose estimation model that represents or otherwise exhibits the likely impact of measurement error with respect to the measured electrical current (isig) input variable. Again, in embodiments where the error mitigation process 400 is being performed with respect to an insight model downstream of the glucose estimation model, the simulated set of measurement values may be input or otherwise provided to the insight model, which, in turn, is utilized to calculate or otherwise determine simulated output data for the insight model as a function of the simulated measurement values and the same values for other input variables to the insight model that were utilized to generate the reference output data for the insight model. Thus, the simulated output data represents or otherwise exhibits the likely impact of measurement error with respect to the lower-level measured electrical current (isig) input variable on the higher-level output of the insight model.

Still referring to FIG. 4, the error mitigation process 400 continues by comparing or otherwise analyzing the relationship between the reference model output and the simulated model output to identify or otherwise determine when the difference between the sets of model outputs is greater than a performance threshold (task 412). When the deviation between the sets of model outputs is greater than the performance threshold, the error mitigation process 400 calculates or otherwise determines a reduction in the weighting or influence to be applied to the input variable in one or more translation models and then updates the translation model(s) in accordance with the reduced weighting for the input variable by reoptimizing the weightings of other input variables (tasks 414, 416). Thereafter, the error mitigation process 400 repeats the steps of determining a reference output for the updated translation model using the reference values for the input variable with the reduced weighting assigned to the input variable, determining a simulated output for the updated translation model using the modulated values for the input variable with the reduced weighting assigned to the input variable, and comparing the simulated output with respect to the reference output (tasks 408, 410, 412). In this manner, the error mitigation process 400 may incrementally or iteratively adjust (e.g., increase or reduce) the weighting of the input variable (e.g., by predetermined or analytically-determined variable incremental values) until the translation model (or combination or sequence thereof) exhibits the desired level of immunity with respect to noise or error in that input variable.

For example, when the translation model of interest is the glucose estimation model to be utilized by the estimation module 306, the remote server 114 may calculate or otherwise determine one or more statistics that characterize the difference between the reference glucose values and the simulated glucose values and then verify or otherwise confirm whether or not the values for those statistics are less than their respective performance thresholds (e.g., task 412). For example, the remote server 114 may calculate percent likelihood of a false positive based on differences between respective contemporaneous pairs of reference and simulated glucose values, and when the false positive metric is greater than an acceptability threshold, the remote server 114 may calculate or otherwise determine an amount by which to reduce the weighting of the measured electrical current (isig) input variable to the glucose estimation model. In this regard, the amount by which to reduce the weighting may be calculated or otherwise determined based on the magnitude of the difference between one or more statistics and their performance thresholds. For example, if the calculated value for the false positive metric is 50% greater than the performance threshold, the remote server 114 may calculate or otherwise determine an updated weighting for the measured electrical current (isig) input variable that is 50% of its previous weighting (e.g., task 414). Thereafter, the remote server 114 may calculate or otherwise determine an updated version of the glucose estimation model that maintains the weighting for the measured electrical current (isig) input variable at the determined reduced weighting value while modifying the weightings of the other input variables to the glucose estimation model to achieve a desired accuracy or reliability for the glucose estimation model using the reduced weighting.

When the translation model of interest is an insight model to be utilized by the insights engine 308, the remote server 114 may similarly calculate or otherwise determine one or more statistics that characterize the difference between the reference output of the insight model and the simulated output of the insight model. For example, when the insight model is a classifier or classification model, the remote server 114 may calculate or otherwise determine a percentage or rate of agreement amongst the reference output and the simulated output (or conversely, a disagreement rate). In this regard, when the agreement rate is less than a threshold agreement rate (or the disagreement rate is greater than a threshold disagreement rate), the remote server 114 determines the difference between the reference output and the simulated output of the insight model exceeds the desired performance threshold(s). In a similar manner as described above, the remote server 114 may calculate or otherwise determine an amount by which to reduce the weighting of the input variable based on the deviation, and then dynamically determine updated versions of the insight model and/or the underlying glucose estimation model used with the insight model using the reduced weighting. In this regard, the updated insight model may weight the glucose measurement values provided by the estimation module 306 differently relative to other input variables to the insight model (e.g., meal data, event log data, and/or the like) than the previous iteration of the insight model (e.g., by either reducing or increasing the influence of the glucose measurement relative to other activity or contextual data). In such embodiments, the weighting of a lower-level input variable input to a lower-level model such as the glucose estimation model may be incrementally and iteratively reduced until achieving respective input variables and corresponding weightings for a combination or sequence of lower-level glucose estimation model and higher-level insight model that achieve a desired measurement error immunity for the higher-level insight model.

After achieving one or more updated translation models that achieve the desired level of error mitigation with respect to a particular input variable of interest, the error mitigation process 400 transmits, provides, or otherwise deploys the updated translation model(s) for future use (task 418). In one or more embodiments, after determining updated glucose estimation models and/or insight models that exhibit improved error immunity, the remote server 114 may automatically push or otherwise provide those models to other devices 102, 106 for use by or at those devices 102, 106. For example, after determining an updated glucose estimation model that reduces the weighting of a particular measurement parameter value output by the digitizer 304, the remote server 114 may automatically push or otherwise transmit the updated estimation module to a sensing device 102, 200 (either directly or via an intermediate client device 106) for implementing the updated glucose estimation model by the estimation module 306 at the sensing device 102, 200. In this regard, previous glucose estimation model data (e.g., input variable weighting factors and the like) that were stored in memory 124, 206 may be overwritten with the updated glucose estimation model data (e.g., updated input variable weighting factors with reduction of the input variable of interest) for subsequent reference by the controller 122, 202 when implementing the estimation module 306 with respect to digital measurement parameter values derived from the output electrical signals of the sensing element 104, 204, 302. Similarly, after determining an updated insight model, the remote server 114 may automatically push or otherwise transmit the updated insight module to a client device 106 for implementing the updated insight model by the insights engine 308 at the client device 106. In this regard, the insights engine 308 may be realized as a feature or component of the client application 108 for providing insights, recommendations, and the like to the patient on his or her client device 106.

Referring to FIG. 4 with reference to FIGS. 1-3, in one or more embodiments, the error mitigation process 400 is performed with respect to a glucose estimation model employed by the estimation module 306. In this regard, for an input variable to the glucose estimation model, such as the measured electrical current (isig), an error profile or error metric associated with the measured electrical current is calculated, derived or otherwise identified from historical measured electrical current data maintained in the database 116 is utilized to generate a modulated set of measured electrical current data based on the set of historical measured electrical current data maintained in the database 116. The historical measured electrical current data functions as reference measured electrical current values that are input or otherwise provided to the glucose estimation model to obtain a reference set of estimated sensor glucose measurement values as a function of the reference measured electrical current values and potentially one or more other input variables (e.g., contemporaneous historical counter electrode voltage values). The modulated set of measured electrical current values are similarly input or otherwise provided to the glucose estimation model to obtain a simulated set of estimated sensor glucose measurement values as a function of the modulated measured electrical current values while using the same contemporaneous values for the other input variable(s) to the glucose estimation model. Thus, the simulated set of estimated sensor glucose measurement values represents the relative effect of noise or error in the measured electrical current input to the glucose estimation model. When a cumulative difference between the simulated set of estimated sensor glucose measurement values and the reference set of estimated sensor glucose measurement values is greater than an acceptability threshold, the glucose estimation model is updated or modified to reduce the difference by reducing the weighting associated with the measured electrical current input variable. For example, the error mitigation process 400 may iteratively scale or otherwise adjust the weighting factor associated with the measured electrical current input variable and iteratively update the glucose estimation model (e.g., tasks 408, 410, 412, 414, 416) until the cumulative difference between the simulated set of estimated sensor glucose measurement values and the reference set of estimated sensor glucose measurement values is less than the acceptability threshold. The resulting updated glucose estimation model with improved noise immunity with respect to the measured electrical current may be automatically pushed or otherwise deployed by the remote server 114 to instances of the sensing device 102, 200 for implementation by the estimation module 306 in lieu of the previous glucose estimation model that exhibited unacceptable noise susceptibility.

Figure 5:
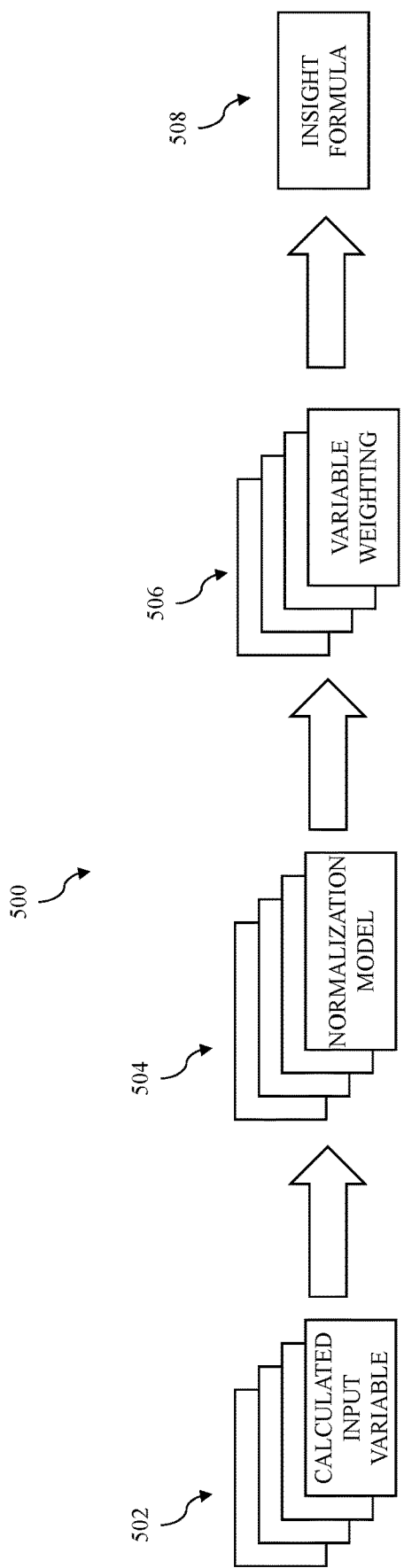
FIG. 5 is a block diagram of an insight model suitable for implementation in the condition analysis system of FIG. 3 in connection with the error mitigation process of FIG. 4 in one or more exemplary embodiments.

FIG. 5 depicts an exemplary block diagram of a patient insight model 500 that may be implemented or otherwise employed by an insights engine 308. The insight model 500 includes a plurality of input variables 502 that are calculated or otherwise determined based on the estimated sensor glucose measurement values output by the estimation module 306. For example, the calculated input variables 502 may include the mean difference between the estimated sensor glucose measurement values and a target glucose value, a time in range percentage calculated based on the percentage or duration of sensor glucose measurement values within a target range of glucose values, the incremental area under the curve (iAUC) calculated based on the estimated sensor glucose measurement values, and so on. Thereafter, the insight model 500 applies a normalization model 504 to each calculated input variable 502 to convert the respective calculated input variable into a normalized value between 0 and 1. The normalized input variable is then scaled or otherwise adjusted by a respective weighting factor 506 before the weighted normalized calculated input variables are input or otherwise provided to an insight formula 508 that calculates or otherwise determines a value the insight metric as a function of the weighted normalized calculated input variables. The calculated insight metric value may then be utilized to score or otherwise classify an aspect of the patient's glycemic condition.

Referring to FIG. 5 with reference to FIGS. 1-3, in one or more embodiments, the error mitigation process 400 may be performed with respect to the insight model 500 employed by the insights engine 308 to adjust the respective variable weighting factor 506 associated with a particular calculated input variable 502. In this regard, an error profile or error metric associated with the sensor glucose measurement values may be calculated, derived or otherwise identified from historical sensor glucose measurement data maintained in the database 116 is utilized to generate a modulated set of sensor glucose measurement data based on the set of historical sensor glucose measurement data maintained in the database 116. The historical sensor glucose measurement values may be utilized to calculate one or more reference values for a calculated input variable 502 of the insight model 500, which, in turn may be utilized to calculate or otherwise determine one or more reference output values of the insight formula 508, for example, by calculating one or more reference values for other input variables 502 from the historical sensor glucose measurement values and applying the respective normalization models 504 and variable weightings 506 to the respective reference calculated input variable values prior to inputting the weighted and normalized reference calculated input variable values to the insight formula 508 to obtain reference output values. Similarly, the modulated sensor glucose measurement values may be utilized to calculate one or more modulated values for a calculated input variable 502 of the insight model 500, which, in turn may be utilized to calculate or otherwise determine one or more simulated output values of the insight formula 508, for example, by calculating one or more reference values for other input variables 502 from the historical sensor glucose measurement values and applying the respective normalization models 504 and variable weightings 506 to the respective calculated input variable values prior to inputting the weighted and normalized calculated input variable values to the insight formula 508 to obtain simulated output values. In this regard, the simulated output of the insight formula 508 represents the impact or effect of the susceptibility of the respective calculated input variable 502 of interest to noise, error, or other variability in the estimated sensor glucose measurements provided by the estimation model 306.

When a cumulative difference between the simulated output values of the insight formula 508 and the reference output values of the insight formula 508 is greater than an acceptability threshold, one or more aspects of the insight model 500 may be adjusted or otherwise modified to reduce the difference. For example, the weighting factor 506 associated with the respective calculated input variable of interest may be scaled or otherwise adjusted to reduce the weighting factor associated with the calculated input variable 502 of interest. The insight model 500 may then be updated to reflect the reduced weighting factor, for example, by using artificial intelligence or other machine learning techniques to vary the equation or function of the insight formula 508 and/or to modify the respective weightings 506 associated with the other calculated input variables to arrive at an updated version of the insight model 500. For example, given the reference input signal and a modulated input signal, the model may be trained to reduce the difference between reference output generated based on the reference input signal and the simulated output generated based on the modulated input signal. In this manner, a machine-learning algorithm may learn to reduce the weighting assigned to the input variables that are the most error prone, thereby reducing the deviation or error between the simulated and reference model outputs. In a similar manner as described above, the respective weighting 506 associated with a calculated variable 502 of interest may be iteratively adjusted, with the other weightings 506 and/or the insight formula 508 being iteratively updated in a corresponding manner (e.g., tasks 408, 410, 412, 414, 416) until the cumulative difference between the simulated insight output and the reference insight output is less than the acceptability threshold. The acceptability threshold may be determined based on the amount of error or difference that results in a change in the resulting output of the insight model (e.g., the amount of error that causes the insight model output to change from "Your meal was good" to "Your meal was not great"). The resulting updated insight model with improved noise immunity with respect to the calculated variable of interest may be automatically pushed or otherwise deployed by the remote server 114 to instances of the sensing device 102, 200 or other devices 106 for implementation by the insights engine 308 in lieu of the previous configuration of the insight model 500 that exhibited unacceptable noise susceptibility.

In other embodiments, additionally or alternatively, the error mitigation process 400 may be performed with respect to the insight model 500 to adjust or otherwise modify the normalization model 504 associated with a respective calculated input variable 502, either independently or in concert with adjusting the weighting factor 506 associated with the respective calculated input variable 502. Additionally, although the foregoing description describes a variable-by-variable analysis implementation of the error mitigation process 400, in practice, the error mitigation process 400 may be implemented in an equivalent manner with respect to all calculated input variables 502 concurrently. For example, the modulated sensor glucose measurement values may be utilized to calculate one or more modulated values for each of the calculated input variables 502 of the insight model 500 before applying the respective normalization models 504 and variable weightings 506 to the modulated input variable values prior to inputting the weighted and normalized modulated input variable values to the insight formula 508 to obtain simulated output values. In such embodiments, the simulated output represents the overall susceptibility of the insight model 500 to noise, error, or other variability in the estimated sensor glucose measurements provided by the estimation model 306 across the range of calculated input variables 502. In such embodiments, the error mitigation process 400 may iteratively adjust one or more of the weighting factors 506, the insight formula 508 and/or the normalization models 504 to arrive at an updated configuration of the insight model 500 that is less susceptible to sensor glucose measurement error or noise across the range of calculated input variables of the insight model 500.

Still referring to FIGS. 1-5, it should be noted that in some embodiments, the error mitigation process 400 may be performed with respect to the glucose estimation model implemented by the estimation model 306 and the insight model 500 concurrently. For example, the error associated with the measured electrical current (isig) input variable to the estimation model 306 may be utilized to arrive at modulated measured electrical current data that may be input to the estimation model 306 to obtain simulated sensor glucose measurement values. The simulated sensor glucose measurement values may then be input to the insight model 500 and utilized to obtain modulated values for one or more calculated input variables 502, which in turn, are utilized to calculate or otherwise derive a simulated output of the insight model 500 that represents the susceptibility of the insight model 500 to noise, error or other variability associated with a lower-level measurement or input variable to the lower-level estimation model 306. In such scenarios, the error mitigation process 400 may be performed by the server 114 to iteratively adjust both the glucose estimation model to be implemented at the estimation model 306 and the insight model 500 in concert with one another until arriving at a configuration of the glucose estimation model and insight model 500 that achieve an output of the insights engine 308 or insight model 500 that exhibits a desired level of immunity to noise, error or other variability with respect to the measured electrical current.

For the sake of brevity, conventional techniques related to glucose sensing and/or monitoring, sampling, filtering, calibration, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A processor-implemented method comprising:
   identifying an error metric associated with an input variable associated with a translation model, the translation model providing an output glucose value that is influenced by a value for the input variable and a weighting applied to the input variable;
   determining a reference output glucose value of the translation model by providing reference input values for the input variable to the translation model;
   generating modulated values for the input variable based on the reference input values using the error metric;
   determining a simulated output glucose value of the translation model by providing the modulated values for the input variable to the translation model;
   updating the translation model with a reduced weighting applied to the input variable when a difference between the simulated output glucose value and the reference output glucose value is greater than a threshold, resulting in an updated translation model which mitigates error associated with the input variable;

providing an output glucose value of the updated translation model based on one or more subsequent values for the input variable derived from one or more electrical signals output by an instance of a sensing element capable of providing electrical signals influenced by glucose levels in a body of a patient; and providing a notification pertaining to a glucose level in the body of the patient, wherein the notification is generated based at least in part on the output glucose value of the updated translation model.

2. The processor-implemented method of claim 1, wherein the translation model comprises an estimation model for providing an estimated glucose value, wherein:

determining the reference output glucose value comprises determining a reference set of measurement glucose values using the reference input values;

determining the simulated output glucose value comprises determining a simulated set of measurement glucose values using the modulated values; and updating the translation model comprises updating the estimation model to reduce the difference between the simulated set of measurement glucose values and the reference set of measurement glucose values by applying the reduced weighting to the input variable in the estimation model.

3. The processor-implemented method of claim 2, wherein:

the sensing element comprises an interstitial glucose sensing arrangement;

the estimation model comprises a sensor glucose estimation model for providing an estimated glucose value;

the reference set of measurement glucose values comprises a reference set of estimated glucose measurement values determined by the sensor glucose estimation model as a function of the reference input values and the weighting applied to the input variable; and the simulated set of measurement glucose values comprises a simulated set of estimated glucose measurement values determined by the sensor glucose estimation model as a function of the modulated values and the weighting applied to the input variable.

4. The processor-implemented method of claim 3, wherein the input variable comprises an output electrical current, an electrode voltage, or an electrochemical impedance spectroscopy (EIS) value determined based on the electrical signals provided by the interstitial glucose sensing arrangement.

5. The processor-implemented method of claim 1, wherein the translation model comprises an insight model for characterizing an aspect of the glucose level in the body of the patient, wherein:

the input variable comprises an estimated value output by an estimation model;

identifying the error metric comprises determining the error metric associated with the estimated value output by the estimation model;

determining the reference output glucose value comprises providing reference values from the estimation model for the input variable to the insight model to obtain reference characterizations for the aspect of the glucose level in the body of the patient;

generating the modulated values comprises determining simulated values for the input variable based on the reference values from the estimation model using the error metric;

determining the simulated output glucose value comprises providing the simulated values for the input variable to the insight model to obtain simulated characterizations for the aspect of the glucose level in the body of the patient;

updating the translation model comprises updating the insight model with the reduced weighting applied to the estimated value output by the estimation model when a difference between the simulated characterizations and the reference characterizations is greater than the threshold; and the notification is generated based at least in part on an output of the updated insight model when one or more subsequent values for an estimated value derived by the estimation model from one or more electrical signals output by the instance of the sensing element are input to the updated insight model with the reduced weighting.

6. The processor-implemented method of claim 5, wherein:

the sensing element comprises an interstitial glucose sensing arrangement; and the estimation model comprises a sensor glucose estimation model for providing an estimated glucose value.

7. The processor-implemented method of claim 1, wherein:

the translation model comprises an insight model for generating the output glucose value based on an aspect of the glucose level in the body of the patient as a function of an estimated value for the glucose level in the body of the patient provided by an estimation model having the weighting applied to the input variable;

determining the reference output glucose value comprises:

determining a reference set of estimated measurement values for the glucose level in the body of the patient as a function of the reference input values using the estimation model; and inputting the reference set of estimated measurement values to the insight model to determine the reference output glucose value as an output of the insight model based at least in part on the reference set of estimated measurement values; and determining the simulated output glucose value comprises:

determining a simulated set of estimated measurement values for the glucose level in the body of the patient as a function of the modulated values using the estimation model; and inputting the simulated set of estimated measurement values to the insight model to determine the simulated output glucose value as an output of the insight model based at least in part on the simulated set of estimated measurement values.

8. The processor-implemented method of claim 7, wherein updating the translation model comprises:

updating the estimation model with the reduced weighting applied to the input variable, resulting an updated estimation model; and updating the insight model for generating the output glucose value as a function of the estimated value for the glucose level in the body of the patient provided by the updated estimation model having the reduced weighting applied to the input variable.

9. The processor-implemented method of claim 7, wherein:

the sensing element comprises an interstitial glucose sensing arrangement;

the estimation model comprises a sensor glucose estimation model for providing an estimated glucose value;

the reference set of estimated measurement values comprises a reference set of estimated glucose measurement values determined by the sensor glucose estimation model as a function of the reference input values and the weighting applied to the input variable;

the simulated set of estimated measurement values comprises a simulated set of estimated glucose measurement values determined by the sensor glucose estimation model as a function of the modulated values and the weighting applied to the input variable; and the input variable is determined based on the electrical signals provided by the interstitial glucose sensing arrangement and comprises an output electrical current, an electrode voltage, or an electrochemical impedance spectroscopy (EIS) value.

10. The processor-implemented method of claim 1, wherein:

the translation model comprises an insight model for generating the output glucose value based on an aspect of the glucose level of the body of the patient as a function of an estimated value for the glucose level of the body of the patient provided by an estimation model and having the weighting applied to the estimated value;

determining the reference output glucose value comprises:
   determining a reference set of estimated measurement values for the glucose level of the body of the patient as a function of the reference input values using the estimation model; and
   inputting the reference set of estimated measurement values to the insight model to determine the reference output glucose value as an output of the insight model based at least in part on the reference set of estimated measurement values;

determining the simulated output glucose value comprises:
   determining a simulated set of estimated measurement values for the glucose level of the body of the patient as a function of the modulated values using the estimation model; and
   inputting the simulated set of estimated measurement values to the insight model to determine the simulated output glucose value as an output of the insight model based at least in part on the simulated set of estimated measurement values; and updating the translation model comprises updating the insight model with the reduced weighting applied to the estimated value for the glucose level of the body of the patient provided by the estimation model.

11. The processor-implemented method of claim 10, wherein the output glucose value is generated based at least in part on an output of the updated insight model when one or more subsequent values for the estimated value provided by the estimation model based on one or more electrical signals output by the instance of the sensing element are input to the updated insight model with the reduced weighting applied to the one or more subsequent values for the estimated value.

12. The processor-implemented method of claim 10, wherein:

the sensing element comprises an interstitial glucose sensing arrangement;

the estimation model comprises a sensor glucose estimation model for providing an estimated glucose value;

the reference set of estimated measurement values comprises a reference set of estimated glucose measurement values determined by the sensor glucose estimation model as a function of the reference input values and the weighting applied to the input variable;

the simulated set of estimated measurement values comprises a simulated set of estimated glucose measurement values determined by the sensor glucose estimation model as a function of the modulated values and the weighting applied to the input variable; and the input variable is determined based on the electrical signals provided by the interstitial glucose sensing arrangement and comprises an output electrical current, an electrode voltage, or an electrochemical impedance spectroscopy (EIS) value.

13. A processor-implemented method comprising:

identifying an error metric associated with an input variable influenced by electrical signals provided by a glucose sensing element, the electrical signals being influenced by a glucose level in a body of a patient;

determining modulated values for the input variable using the error metric;

determining a reference output glucose value of a translation model using reference input values for the input variable, wherein the reference output glucose value of the translation model is influenced by the reference input values and a weighting applied to the input variable;

determining a simulated output glucose value of the translation model using the modulated values for the input variable, wherein the simulated output glucose value of the translation model is influenced by the modulated values for the input variable and the weighting;

when a difference between the simulated output glucose value and the reference output glucose value is greater than a threshold, updating, by one or more processors, the translation model with a reduced weighting applied to the input variable, resulting in an updated translation model which mitigates error associated with the input variable; and providing the updated translation model to a device monitoring the glucose level in the body of the patient using the glucose sensing element, wherein the device generates an output glucose value of the updated translation model based on one or more subsequent values for the input variable derived from one or more subsequent electrical signals output by the glucose sensing element in response to the glucose level in the body of the patient, wherein the device provides a notification pertaining to a glucose level in the body of the patient, the notification generated based at least in part on the output glucose value of the updated translation model.

14. The processor-implemented method of claim 13, wherein:

the translation model comprises an insight model;

the input variable comprises a sensor glucose measurement input to the insight model;

the translation model provides an output glucose value that is influenced by an intermediate variable calculated based on the sensor glucose measurement;

the weighting comprises a weighting factor applied to the intermediate variable; and updating the translation model comprises reducing the weighting factor.

15. The processor-implemented method of claim 14, wherein:

the reference input values comprise a reference set of sensor glucose measurement data;

determining the modulated values comprises determining a modulated set of sensor glucose measurement data based on the reference set of sensor glucose measurement data and the error metric associated with the sensor glucose measurement;

determining the reference output glucose value comprises the translation model providing the reference output glucose value based at least in part on the weighting factor applied to one or more reference values for the intermediate variable calculated based on the reference set of sensor glucose measurement data; and determining the simulated output glucose value comprises the translation model providing the simulated output glucose value based at least in part on the weighting factor applied to one or more modulated values for the intermediate variable calculated based on the modulated set of sensor glucose measurement data.

16. The processor-implemented method of claim 15, wherein updating the translation model comprises:
iteratively reducing the weighting factor,
iteratively determining an updated reference output based at least in part on the reduced weighting factor applied to the one or more reference values for the intermediate variable, and
iteratively determining an updated simulated output based at least in part on the reduced weighting factor applied to the one or more modulated values for the intermediate variable until the difference between the simulated output glucose value and the reference output glucose value is less than the threshold.

17. The processor-implemented method of claim 13, wherein:
the input variable comprises a digital measurement parameter determined based at least in part on the electrical signals;
the translation model comprises a glucose estimation model providing an estimated sensor glucose measurement value based at least in part on the digital measurement parameter and a weighting factor applied to the digital measurement parameter; and
updating the translation model comprises reducing the weighting factor applied to the digital measurement parameter.

18. The processor-implemented method of claim 17, wherein:
the reference input values comprise a reference set of values for the digital measurement parameter;
determining the modulated values comprises determining a modulated set of values for the digital measurement parameter based on the reference set of values and the error metric associated with the digital measurement parameter;
determining the reference output glucose value comprises determining reference sensor glucose measurement data as a function of the reference set of values using the glucose estimation model; and
determining the simulated output glucose value comprises determining simulated sensor glucose measurement data as a function of the modulated set of values using the glucose estimation model.

19. The processor-implemented method of claim 18, wherein updating the translation model comprises:
iteratively reducing the weighting factor, iteratively determining an updated glucose estimation model with the reduced weighting factor applied to the digital measurement parameter,
iteratively determining updated sensor glucose measurement data as a function of the reference set of values using the updated glucose estimation model with the reduced weighting factor applied to the digital measurement parameter, and
iteratively determining updated simulated sensor glucose measurement data as a function of the modulated set of values using the updated glucose estimation model with the reduced weighting factor applied to the digital measurement parameter until the difference between the simulated output glucose value and the reference output glucose value is less than the threshold.

20. A system comprising:
a database configured to store historical measurement data corresponding to instances of a sensing element influenced by a glucose level in a body of a patient; and
a server coupled to the database, the server configured to identify an error metric associated with an input variable to a translation model based at least in part on the historical measurement data, identify reference input values for the input variable using the historical measurement data, determine modulated values for the input variable based on the reference input values using the error metric, determine a reference output glucose value of the translation model by providing the reference input values for the input variable to the translation model, determine a simulated output glucose value of the translation model by providing the modulated values for the input variable to the translation model, update the translation model to reduce a weighting applied to the input variable when a difference between the simulated output glucose value and the reference output glucose value is greater than a threshold, the updated translation model mitigating error associated with the input variable, provide an output glucose value of the updated translation model based on one or more subsequent values for the input variable derived from one or more electrical signals output by an instance of the sensing element, and providing a notification pertaining to a glucose level in the body of the patient, wherein the notification is generated based at least in part on the output glucose value of the updated translation model.

* * * * *